(12) United States Patent
Kuwahara

(10) Patent No.: US 11,262,443 B2
(45) Date of Patent: Mar. 1, 2022

(54) INFORMATION PROCESSING APPARATUS AND DETECTION APPARATUS

(71) Applicant: Socionext Inc., Kanagawa (JP)

(72) Inventor: Yuji Kuwahara, Yokohama (JP)

(73) Assignee: SOCIONEXT INC., Kanagawa (JP)

(*) Notice: Subject to any disclaimer, the term of this patent is extended or adjusted under 35 U.S.C. 154(b) by 229 days.

(21) Appl. No.: 16/555,937

(22) Filed: Aug. 29, 2019

(65) Prior Publication Data

US 2019/0383928 A1 Dec. 19, 2019

Related U.S. Application Data

(63) Continuation of application No. PCT/JP2017/020042, filed on May 30, 2017.

(51) Int. Cl.
 *G01S 7/35* (2006.01)
 *G01S 13/56* (2006.01)
 *G01S 13/536* (2006.01)

(52) U.S. Cl.
 CPC .............. *G01S 13/56* (2013.01); *G01S 7/352* (2013.01); *G01S 13/536* (2013.01); *G01S 7/356* (2021.05)

(58) Field of Classification Search
 CPC ..... A61B 5/113; G01S 13/343; G01S 13/536; G01S 13/56; G01S 13/88; G01S 7/352; G01S 7/414; G01S 7/415; G01S 7/356
 See application file for complete search history.

(56) References Cited

U.S. PATENT DOCUMENTS

| | | | |
|---|---|---|---|
| 2010/0076514 A1* | 3/2010 | Cho | A61B 5/0205 607/18 |
| 2013/0079647 A1* | 3/2013 | McGonigle | A61B 5/7239 600/500 |
| 2013/0135173 A1 | 5/2013 | Ridgeway | |

(Continued)

FOREIGN PATENT DOCUMENTS

| | | |
|---|---|---|
| JP | H11-118913 A | 4/1999 |
| JP | 2013-072865 A | 4/2013 |
| JP | 2016-135194 A | 7/2016 |

(Continued)

OTHER PUBLICATIONS

International Search Report and Written Opinion issued in corresponding International Patent Application No. PCT/JP2017/020042, dated Sep. 5, 2017, with partial translation.

(Continued)

*Primary Examiner* — Timothy A Brainard
(74) *Attorney, Agent, or Firm* — McDermott Will and Emery LLP

(57) ABSTRACT

An information processing apparatus includes a calculation unit configured to calculate distance spectra based on a beat signal being a difference between a transmitted wave, which is a radio wave that is transmitted by a sensor and that is swept in frequency, and a reflected wave of the transmitted wave, the reflected wave being received by the sensor, and configured to calculate one or more time-sequenced waveforms each indicating time changes in intensity of the distance spectra with respect to respective distances from the sensor, and a detection unit configured to detect respiration of a living organism based on the one or more time-sequenced waveforms.

11 Claims, 15 Drawing Sheets

(56) References Cited

U.S. PATENT DOCUMENTS

2016/0022204 A1* 1/2016 Mostov ............... A61B 5/0002
600/301
2018/0078212 A1* 3/2018 Brumfield ........... A61B 5/0816

FOREIGN PATENT DOCUMENTS

JP        2016-156751 A    9/2016
WO     2016/195113 A1   12/2016

OTHER PUBLICATIONS

Notice of Reasons for Refusal, dated Oct. 13, 2020 issued in corresponding Japanese Patent Application No. 2019-521563; with English translation.

Notification of the First Office Action, dated Sep. 1, 2021 issued in corresponding Chinese Patent Application No. 201780089182.6; with English translation.

\* cited by examiner

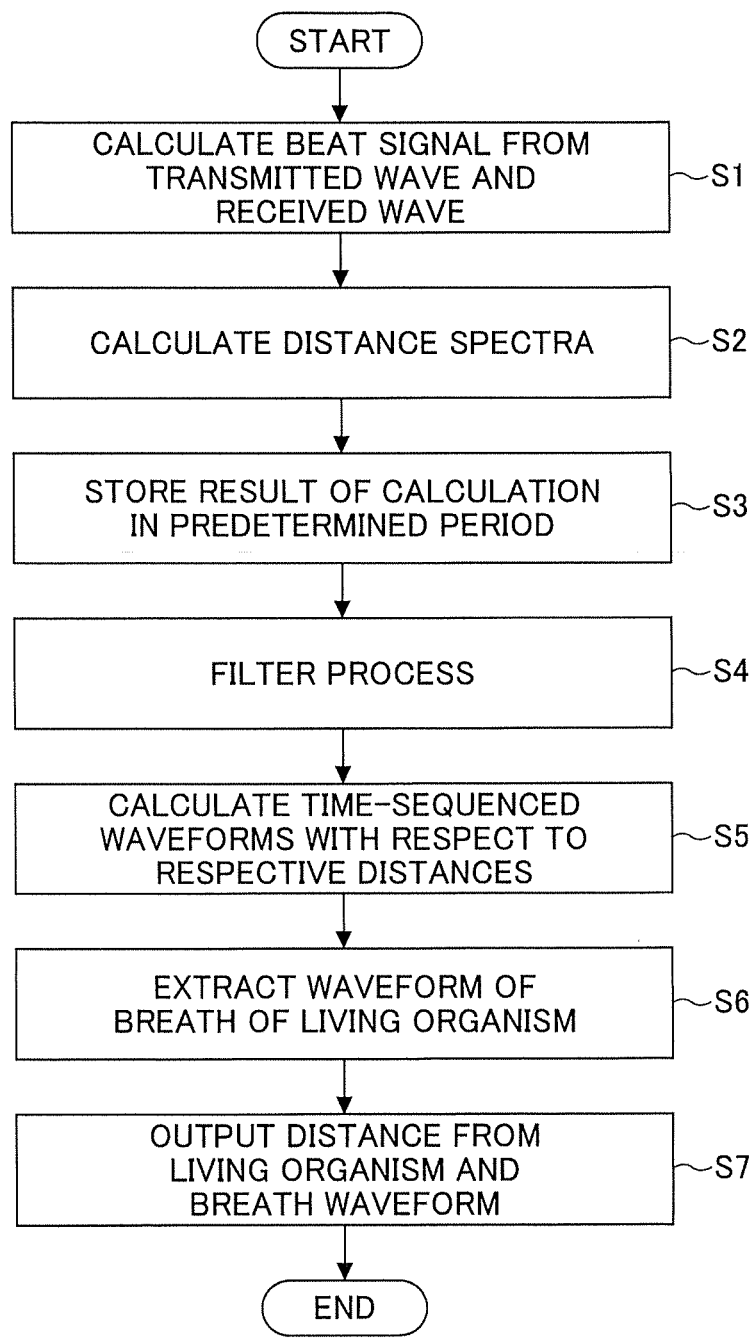

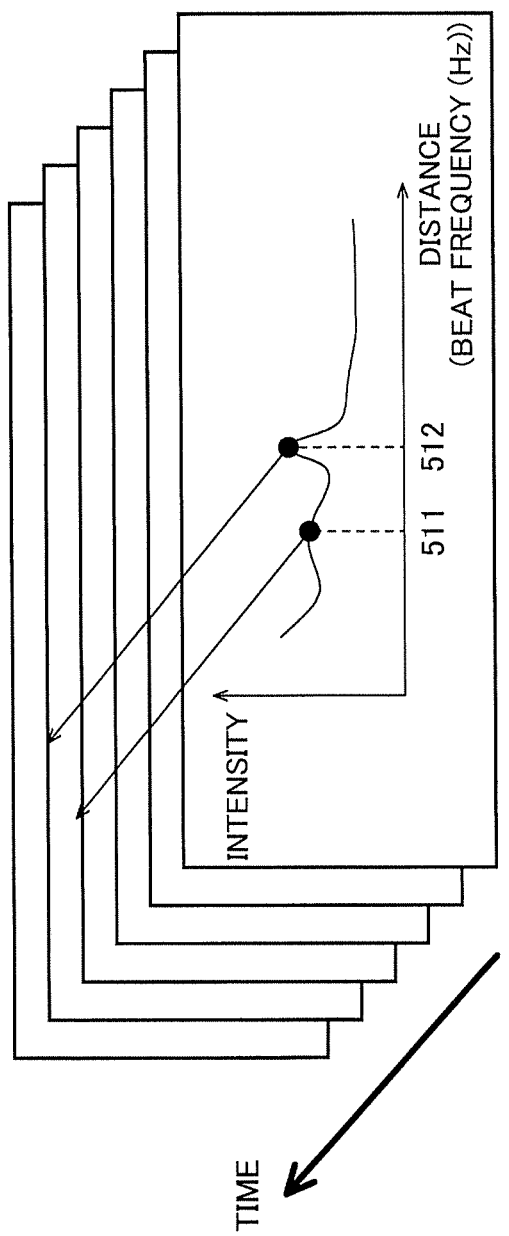

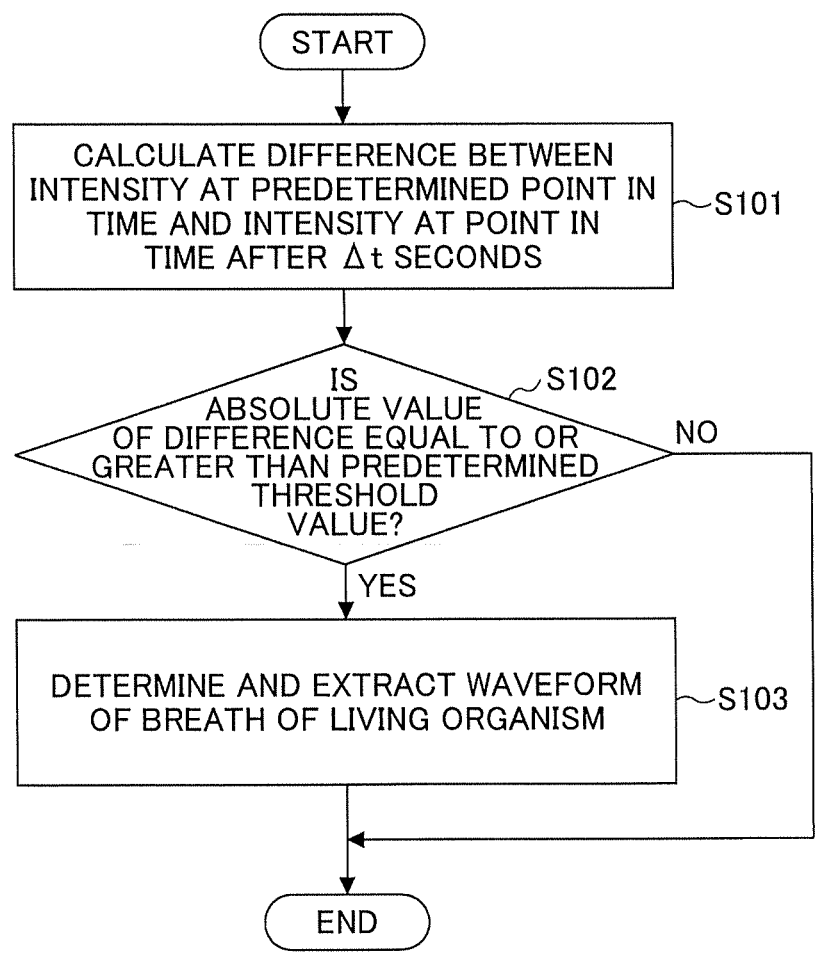

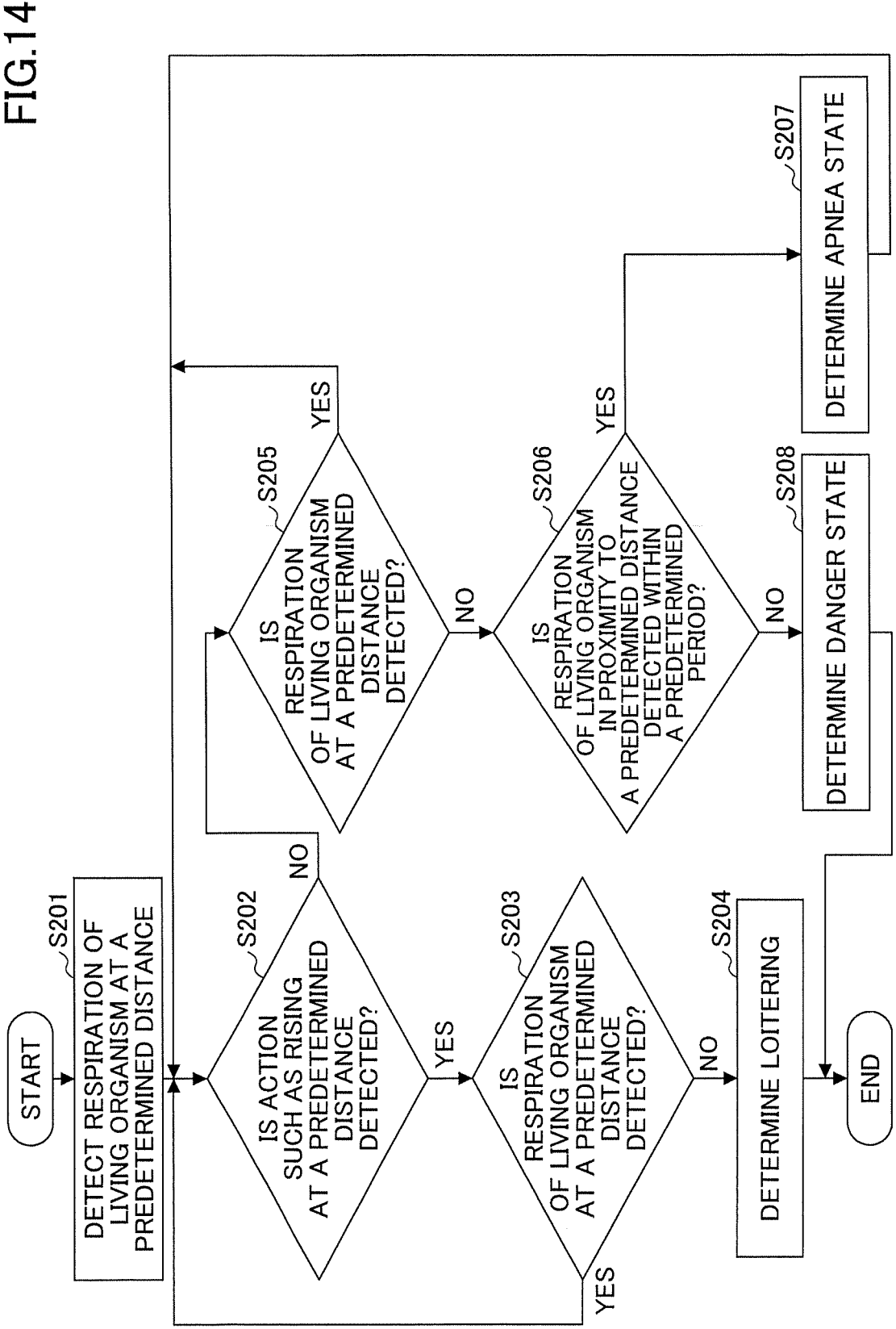

INFORMATION PROCESSING APPARATUS AND DETECTION APPARATUS

CROSS-REFERENCE TO RELATED APPLICATION

This application is a continuation application of International Application No. PCT/JP2017/020042 filed on May 30, 2017, and designated the U.S., the entire contents of which are incorporated herein by reference.

BACKGROUND OF THE INVENTION

1. Field of the Invention

The present disclosure relates to an information processing apparatus and a detection apparatus.

2. Description of the Related Art

Techniques that use an FM-CW (Frequency Modulated Continuous Wave) radar sensor to measure a distance between a person and an object have been known. Such an FM-CW radar sensor uses, as a transmitted wave, a frequency-swept radio wave, calculates a beat frequency being a difference between frequencies of the transmitted wave and a reflected wave, and calculates a distance from the sensor to an object to be measured, based on the calculated beat frequency.

Further, techniques that use the FM-CW radar sensor to detect respiration of a living organism are known (see, e.g., Japanese Unexamined Patent Application Publications No. 2016-135194 and No. 2016-156751).

SUMMARY OF THE INVENTION

In one aspect, an information processing apparatus is provided, including a calculation unit configured to calculate distance spectra based on a beat signal being a difference between a transmitted wave, which is a radio wave that is transmitted by a sensor and that is swept in frequency, and a reflected wave of the transmitted wave, the reflected wave being received by the sensor, and configured to calculate one or more time-sequenced waveforms each indicating time changes in intensity of the distance spectra with respect to respective distances from the sensor, and a detection unit configured to detect respiration of a living organism based on the one or more time-sequenced waveforms.

According to one aspect, it is possible to improve detection accuracy of a living organism.

BRIEF DESCRIPTION OF THE DRAWINGS

FIG. 6 is a flowchart illustrating an example of processing by the detection apparatus;

FIGS. 7A to 7C are diagrams for explaining time-sequenced waveforms with respect to respective distances;

FIG. 8 is a flowchart illustrating an example of a process of extracting a time-sequenced waveform of the breath of a living organism:

FIG. 14 is a flowchart illustrating an example of processing by the detection apparatus;

DESCRIPTION OF THE PREFERRED EMBODIMENTS

The techniques known to the inventors have a problem that may detect, as a living organism, a non-living object such as furniture, general merchandise, a wall, a floor, or a ceiling.

Also, for example, if there exists a water tank, a drinking container, or the like in the surroundings of a living organism to be measured, a reflected wave from water becomes relatively large depending on a frequency of a transmitted wave. Accordingly, determination of the presence or absence of breathing may be made erroneously.

In view of the point recognized by the inventors, an objective with regard to one aspect is to provide a technique capable of improving detection accuracy of a living organism.

First Embodiment

With reference to the drawings, explanation will be provided hereinafter for embodiments according to the present disclosure.

<Whole Configuration>

Figure 1:
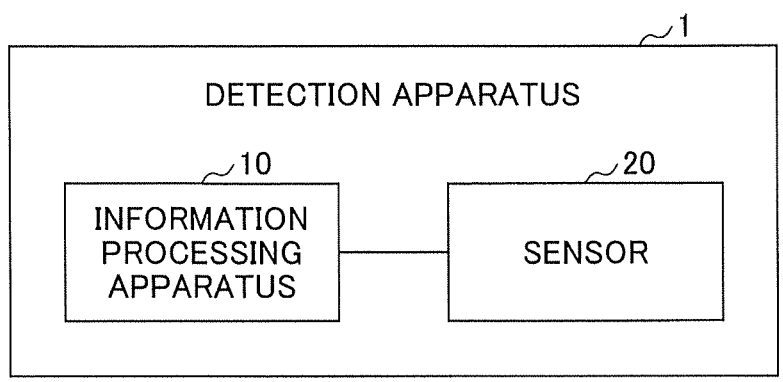
FIG. 1 is a diagram illustrating an example of a configuration of a detection apparatus according to an embodiment.

FIG. 1 is a diagram illustrating an example of a configuration of a detection apparatus 1 according to an embodiment. In FIG. 1, the detection apparatus 1 includes an information processing apparatus 10 and a sensor 20.

The information processing apparatus 10 is a PC (Personal Computer), an embedded system, or the like, for example.

The sensor 20 is an FM-CW radar sensor, for example. For example, the sensor 20 may be implemented by an integrated circuit that is formed on a semiconductor substrate.

The information processing apparatus 10 and the sensor 20 are connected via a bus or the like, for example.

Based on a signal obtained by the sensor 20, the information processing apparatus 10 detects the presence or absence of a living organism and a distance from a living organism, as well as a respiratory status of a living organism, etc.

<Hardware Configuration>

<<Information Processing Apparatus>>

Figure 2:
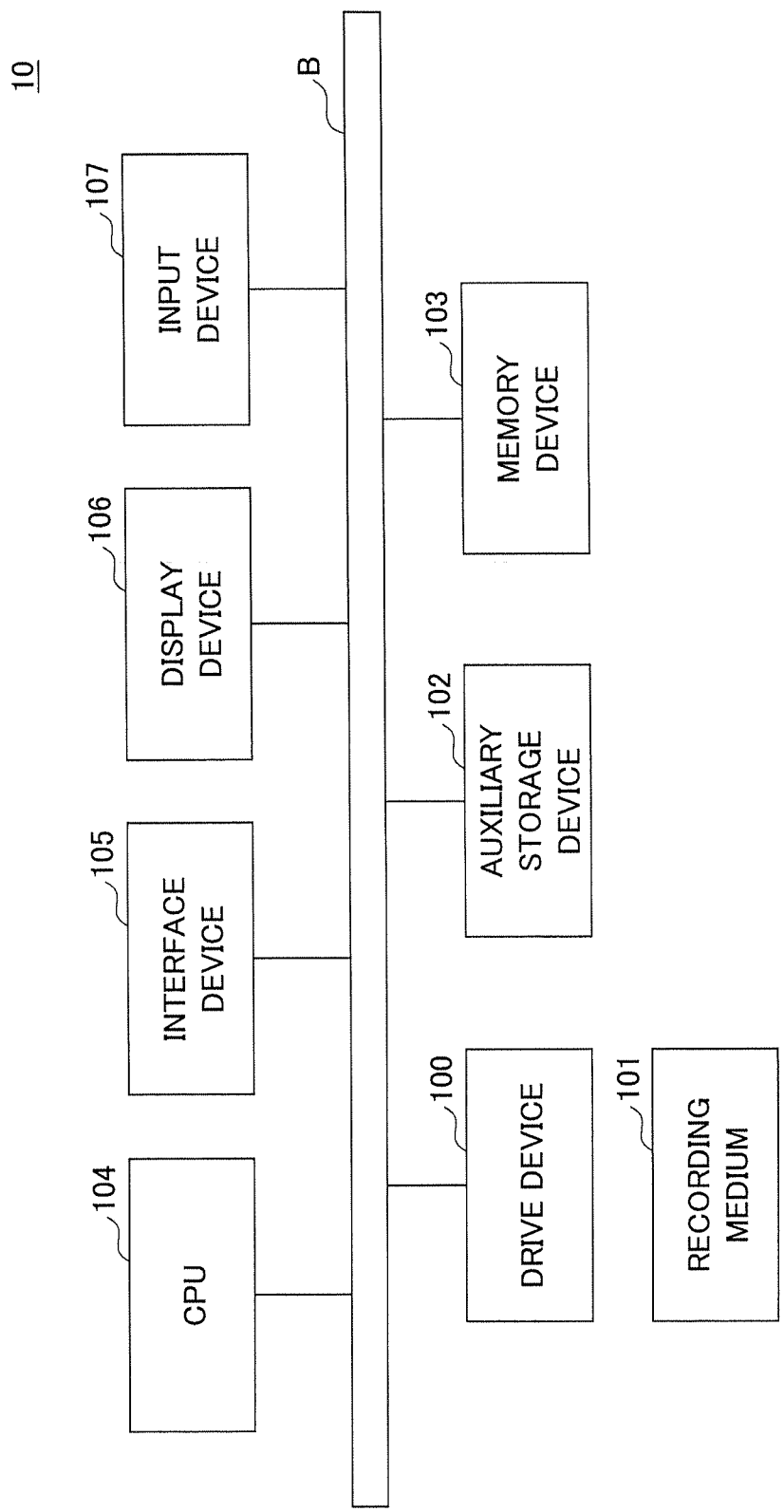
FIG. 2 is a diagram illustrating an example of a hardware configuration of an information processing apparatus according to the embodiment.

FIG. 2 is a diagram illustrating an example of a hardware configuration of the information processing apparatus 10 according to the embodiment. The information processing apparatus 10 of FIG. 2 includes a drive device 100, an auxiliary storage device 102, a memory device 103, a CPU 104, an interface device 105, a display device 106, an input device 107, and the like, which are interconnected via a bus B.

An information processing program that implements processing by the information processing apparatus 10 is provided by a recording medium 101. When the recording medium 101 storing the information processing program is set in the drive device 100, the information processing program is installed on the auxiliary storage device 102 from the recording medium 101 through the drive device 100. However, the information processing program is not always required to be installed through the recording medium 101, and may be downloaded from another computer via a network. The auxiliary storage device 102 stores the installed information processing program, as well as storing necessary file(s), data, and the like.

The memory device 103 retrieves a program from the auxiliary storage device 102 to store the program, when an instruction to boot a program is received. The CPU 104 implements a function for use in the information processing apparatus 10 according to the program stored in the memory device 103. The interface device 105 is used as an interface for connecting to a network. The display device 106 displays a programmed GUI (Graphical User Interface) and the like. The input device 107 includes a touch panel, button(s) and the like, and is used to cause various operating instructions to be inputted.

Note that a portable recording medium such as a CD-ROM, a DVD disk, or a USB memory is an example of the recording medium 101. Also, an HDD (Hard Disk Drive), a flash memory, or the like is an example of the auxiliary storage device 102. Each of the recording medium 101 and the auxiliary storage device 102 corresponds to a computer readable recording medium.

<<Sensor>>

Figure 3:
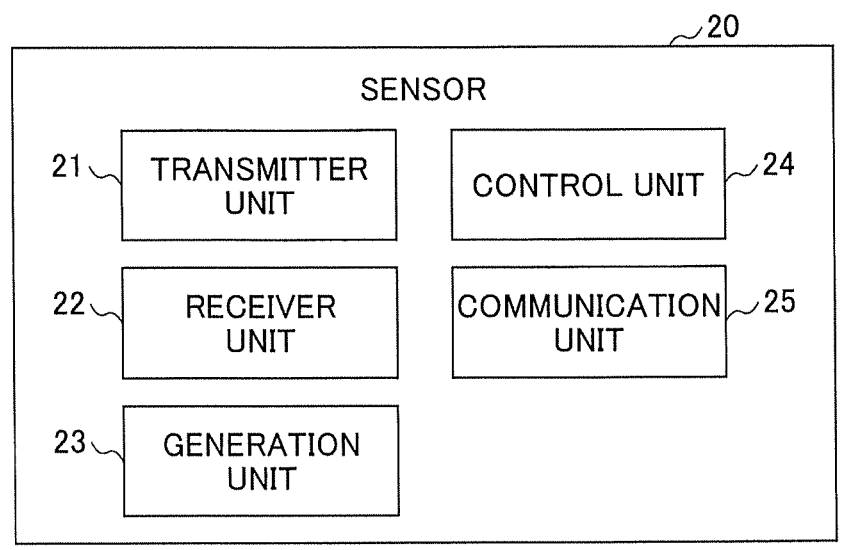
FIG. 3 is a diagram illustrating an example of a hardware configuration of a sensor according to the embodiment.

FIG. 3 is a diagram illustrating an example of a hardware configuration of the sensor 20 according to the embodiment. The sensor 20 in FIG. 3 includes a transmitter unit 21, a receiver unit 22, a generation unit 23, a control unit 24, a communication unit 25, and the like.

The transmitter unit 21 transmits a transmitted wave being a radio wave that is swept in frequency.

The receiver unit 22 receives a reflected wave (received wave) reflected by a living organism, the living organism reflecting the transmitted wave by the transmitter unit 21.

The generation unit 23 generates a beat signal indicative of a beat frequency that is a difference between frequencies of a transmitted wave transmitted by the transmitter unit 21 and a received wave received by the receiver unit 22.

The control unit 24 controls the entire sensor 20 such as the transmitter unit 21, the receiver unit 22, the generation unit 23, and the communication unit 25.

The communication unit 25 communicates with the information processing apparatus 10. For example, the communication unit 25 indicates, to the information processing apparatus 10, a real-time beat signal indicative of a beat frequency at each point in time generated by the generation unit 23.

<Functional Configuration>

Figure 4:
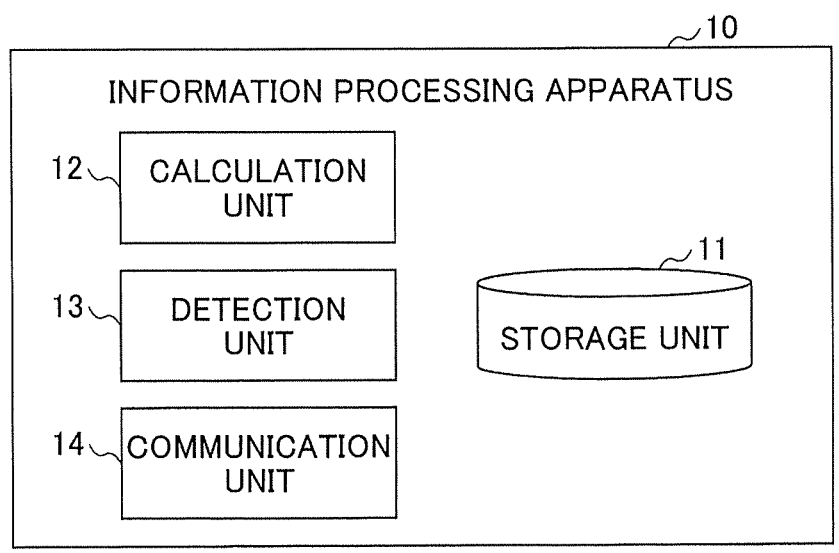
FIG. 4 is a diagram for explaining a functional configuration of the information processing apparatus.

Hereafter, a functional configuration of the information processing apparatus 10 is described with reference to FIG. 4. As an example, FIG. 4 is a functional block diagram of the information processing apparatus 10 according to the embodiment.

The information processing apparatus 10 includes a storage unit 11. The storage unit 11 is implemented by using the auxiliary storage device 102 or the like, for example.

The storage unit 11 stores data or the like calculated by a calculation unit 12, for example.

Further, the information processing apparatus 10 includes the calculation unit 12, a detection unit 13, and a communication unit 14. Each of these units is implemented by one or more programs that are installed on the information processing apparatus 10 and that cause the CPU 104 of the information processing apparatus 10 to execute a process.

The calculation unit 12 uses a Fourier transform of a beat signal obtained by the sensor 20 to calculate spectral intensity (distance spectrum) with respect to each distance from the sensor 20. Further, the calculation unit 12 calculates data of a waveform (which is hereinafter referred to as a "time-sequenced waveform") indicating time changes of intensity of the distance spectrum with respect to each distance.

The detection unit 13 detects respiration of a living organism based on time-sequenced waveform(s) calculated by the calculation unit 12. The detection unit 13 also detects a movement of a living organism or a respiratory arrest state of a living organism, based on a given time-sequenced waveform with respect to a distance at which respiration of the living organism is detected.

The communication unit 14 sends a predetermined notification to an external device or the like, based on information detected by the detection unit 13.

<Principle of FM-CW Radar>

Figure 5:
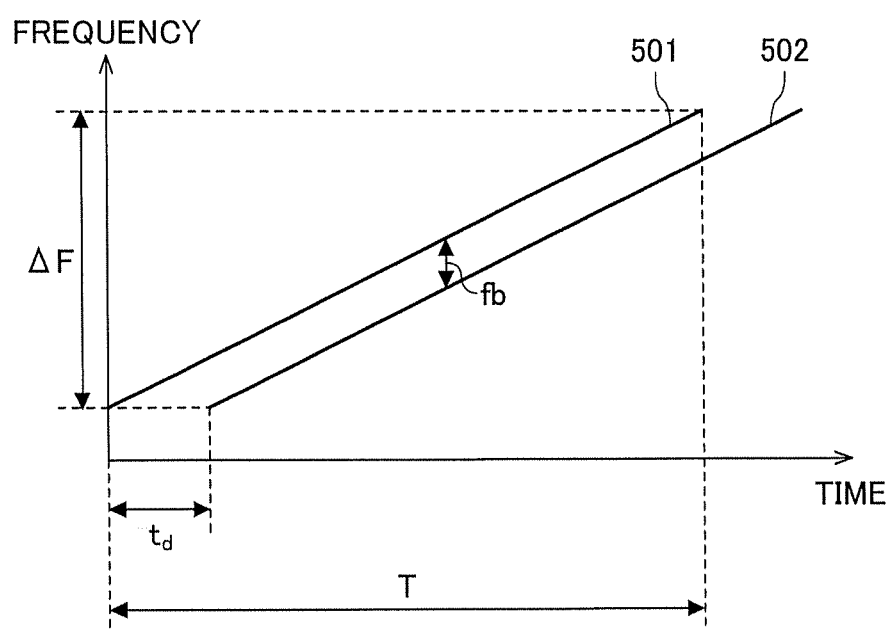
FIG. 5 is a diagram for explaining a transmitted wave and a received wave that the sensor transmits and receives.

Hereafter, a principle of processing by the sensor 20 for an FM-CW radar is described with reference to FIG. 5. FIG. 5 is a diagram for explaining a transmitted wave and a received wave that the sensor 20 transmits and receives.

The sensor 20 is the so-called sensor for an FM-CW radar, and transmits a frequency-swept radio wave, as a transmitted wave 501. The sensor 20 then outputs, to the information processing apparatus 10, a beat signal indicative of a beat frequency $f_b$ that is a difference between frequencies of the transmitted wave 501 and a received wave 502.

The relationship with respect to the beat frequency $f_b$, a swept width $\Delta F$ of a frequency used with the transmitted wave 501, a modulation period $T$, and a round-trip delay time $t_d$ until the transmitted wave 501 is received as the received wave 502 is given by Formula (1) below.

$$f_b/t_d = \Delta F/T \tag{1}$$

The relationship with respect to the round-trip delay time $t_d$, the light speed $c$, and a distance $R$ between an object such as a living organism, which reflects the transmitted wave 501, and the sensor 20 is given by Formula (2) below.

$$t_d = 2R/c \tag{2}$$

Accordingly, Formulas (1) and (2) derive Formula (3) below.

$$f_b = \Delta F 2R/Tc \tag{3}$$

Accordingly, a beat frequency $f_b$ affected by an object of which the distance R from the sensor 20 is relatively short is relatively low, and a beat frequency $f_b$ affected by an object of which the distance R from the sensor 20 is relatively long is relatively high. In light of the above point, the information processing apparatus 10 can calculate a distance to each object based on a waveform indicative of the beat frequency $f_b$ affected by each object, the waveform being obtained by the sensor 20. Note that the Doppler effect causes a decreased change in the beat frequency $f_b$ affected by an object that moves away from the sensor 20. Further, the Doppler effect causes an increased change in the beat frequency $f_b$ affected by an object that moves towards the sensor 20. Accordingly, the velocity of an object is also able to be calculated based on the change in the beat frequency $f_b$.

<Processing>

Hereafter, processing by the detection apparatus 1 is described with reference to FIG. 6. FIG. 6 is a flowchart illustrating an example of processing by the detection apparatus 1.

First, in step S1, the generation unit 23 of the sensor 20 generates a beat signal indicative of a beat frequency being a difference between a transmitted frequency of a transmitted wave and a received frequency of a received wave, based on the transmitted wave transmitted by the transmitter unit 21 and the received wave received by the receiver unit 22.

Next, the calculation unit 12 of the information processing apparatus 10 uses a fast Fourier transform (FFT) of a generated beat signal to calculate spectral intensities (distance spectra) with respect to respective distances from the sensor 20, the respective distances corresponding to frequencies (step S2).

Subsequently, the calculation unit 12 of the information processing apparatus 10 causes the storage unit 11 to store calculated distance spectra in a predetermined period (step S3).

Subsequently, the calculation unit 12 of the information processing apparatus 10 calculates time-sequenced waveforms with respect to respective distances (each sample point in a distance direction, Index) based on the distance spectra in the predetermined period. The calculation unit 12 executes a filter process of the calculated time-sequenced waveforms to remove noise or the like (step S4). As an example, a filter process such as a DC (Direct Current) cut, a low pass filter (Low-pass filter, LPF), or a linear DC cut may be executed. Note that such a filter process may not be executed.

Subsequently, the calculation unit 12 of the information processing apparatus 10 calculates time-sequenced waveforms with respect to the respective distances after the filter process, and causes the storage unit 11 to store such waveforms (step S5).

Subsequently, the detection unit 13 of the information processing apparatus 10 extracts a time-sequenced waveform of the breath of a living organism from the time-sequenced waveforms with respect to the respective distances (step S6).

Subsequently, the detection unit 13 of the information processing apparatus 10 respectively outputs, as a distance from a living organism and a time-sequenced waveform of the breath of a living organism, a distance corresponding to the extracted time-sequenced waveform and the extracted time-sequenced waveform (step S7). The detection unit 13 may cause the distance or/and the time-sequenced waveform to be displayed on a screen or the like.

FIG. 7 is a diagram for explaining time-sequenced waveforms with respect to respective distances. As an example, FIG. 7A illustrates distance spectra at respective points in time of being measured in a predetermined period in step S3. In the example of FIG. 7A, a horizontal axis relates to a distance from the sensor 20 (a distance corresponding to a frequency used with a beat frequency), and a vertical axis relates to intensity with respect to a given beat frequency.

Figure 7B:
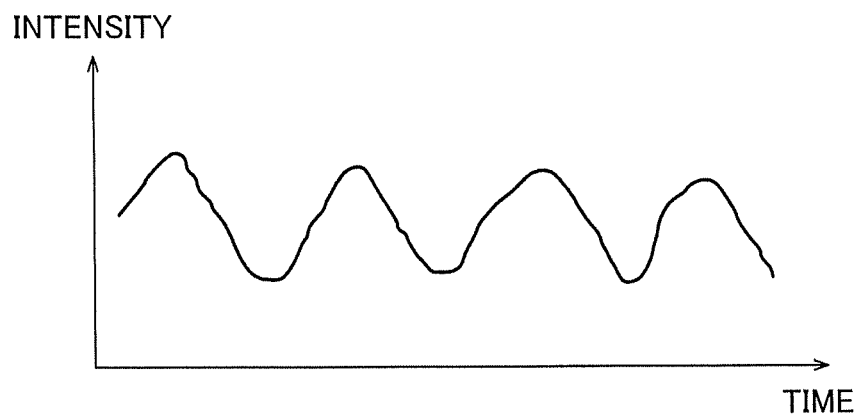
Figure 7C:
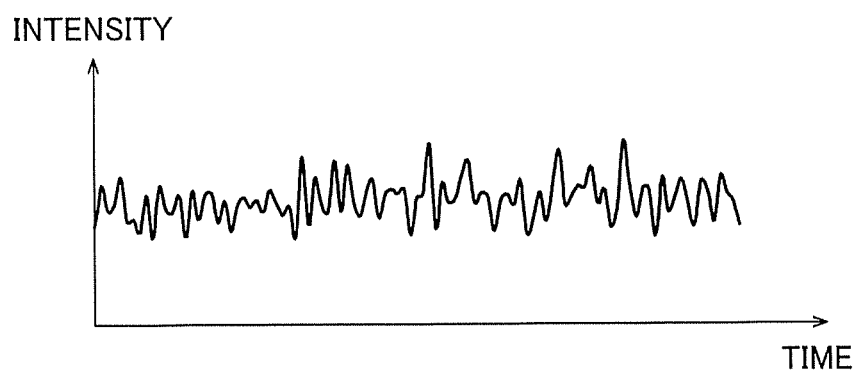

As an example, in FIGS. 7B and 7C, respective time-sequenced waveforms with respect to distances 511 and 512 in the distance spectra in FIG. 7A in step S5 are indicated. FIG. 7B illustrates an example of a time-sequenced waveform of the breath of a living organism. In a process in step S7, the distance 511 and data of the waveform illustrated in FIG. 7B are outputted. With respect to distance spectra, at a certain distance at which a living organism is present, the distance between the sensor 20 and the living organism changes in accordance with the chest of the living organism repeatedly expanding and contracting. For this reason, as illustrated in FIG. 7B, intensity in accordance with a beat frequency indicates time changes.

On the other hand, FIG. 7C illustrates an example of a time-sequenced waveform affected by noise. For example, with respect to a water tank, a wall, furniture, or the like, the distance from the sensor 20 does not change periodically. For this reason, intensity in accordance with a beat frequency indicates less of a change than a living organism. A cycle of changes or the like is also different from that or the like in the breath of a living organism. In view of the above point, in the embodiment, waveforms each indicating time changes in intensity with respect to beat frequencies that correspond to respective distances are obtained to be stored, so that a waveform that satisfies a predetermined condition is detected as a breath waveform of a living organism.

Figure 9:
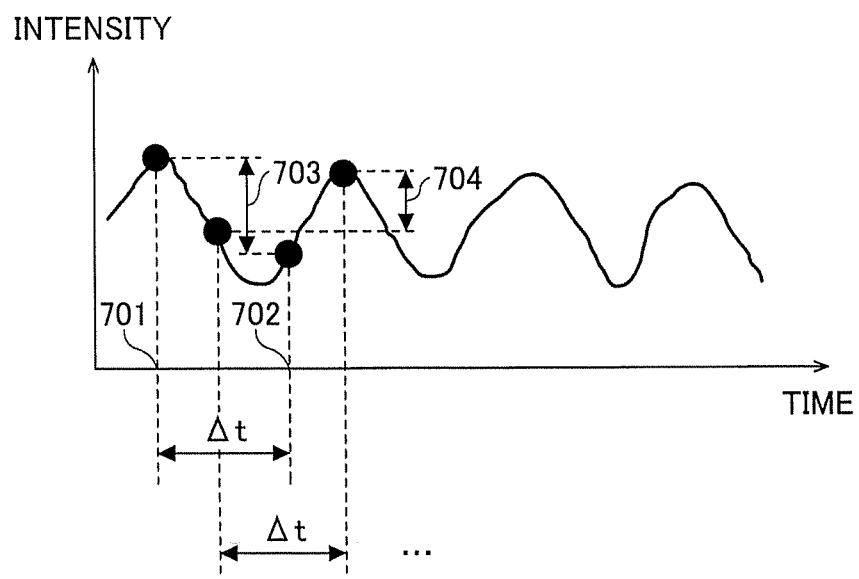
FIG. 9 is a diagram for explaining an example of a process of extracting a time-sequenced waveform of the breath of a living organism.

Example 1 for Extraction of a Time-Sequenced Waveform of the Breath of a Living Organism Hereafter, with reference to FIGS. 8 and 9, a process of extracting, by the detection unit 13, a time-sequenced waveform of the breath of a living organism in step S6 is described, by way of example. FIG. 8 is a flowchart illustrating an example of a process of extracting a time-sequenced waveform of the breath of a living organism. FIG. 9 is a diagram for explaining an example of a process of extracting a time-sequenced waveform of the breath of a living organism. In the following, a certain distance among distances in respective distance spectra is referred to as a distance to be processed. The following process is executed for time-sequenced waveform(s) being waveform(s) each indicating time changes in intensity of beat frequencies corresponding to respective distances in distance spectra.

In step S101, for a given time-sequenced waveform with respect to a distance to be processed, the detection unit 13 calculates a difference between intensity at a predetermined point in time and intensity at a point in time after Δt second(s) from the predetermined point in time.

Subsequently, the detection unit 13 determines whether or not an absolute value of the calculated difference is equal to or greater than a predetermined threshold value (step S102).

When an absolute value of the calculated difference is not equal to or greater than a predetermined threshold value (NO in step S102), the process is finished.

When an absolute value of the calculated difference is equal to or greater than a predetermined threshold value (YES in step S102), the detection unit 13 determines that the time-sequenced waveform is a time-sequenced waveform of the breath of a living organism to extract it (step S103), and finishes the process. In step S103, the detection unit 13 may make determination based on only a difference 703 between intensity at a predetermined point 701 in time (an example of a "first point in time") in FIG. 9 and intensity at a point 702 in time (an example of a "second point in time") after Δt second(s) from the predetermined point in time. Alternatively, the detection unit 13 repeatedly executes the process in step S102 with a predetermined period. When a difference in each period is equal to or greater than a threshold value, the detection unit 13 may determine a time-sequenced waveform of the breath of a living organism to extract it.

Alternatively, when a value through a sum total of each absolute value of a difference in a predetermined period is equal to or greater than a predetermined threshold, a time-sequenced waveform of the breath of a living organism may be determined and be extracted. In this case, each of differences 703 (an example of a "first value"), 704 (an example of the "second value"), ... between intensity at a given point in time and intensity at a point in time after Δt second(s) from the given point in time in a predetermined period is calculated, and when a value through a sum total of each of differences 703, 704, ... is equal to or greater than a threshold value, a time-sequenced waveform of the breath of a living organism may be determined and be extracted.

Note that when it is determined that time-sequenced waveforms with respect to respective distances are each time-sequenced waveforms of the breath of a corresponding living organism, only a time-sequenced waveform with respect to a closest distance to the sensor 20 may be extracted as a time-sequenced waveform of the breath of a living organism. Thereby, for example, in a case where many persons are present side by side, respiration of a person closest to the sensor 20 can be captured. Note that in the conventional art, in a case where many people are present side by side, since interfering breath waveforms are detected, a time-sequenced waveform with respect to a closest distance to the sensor 20 can not be easily extracted.

Figure 10:
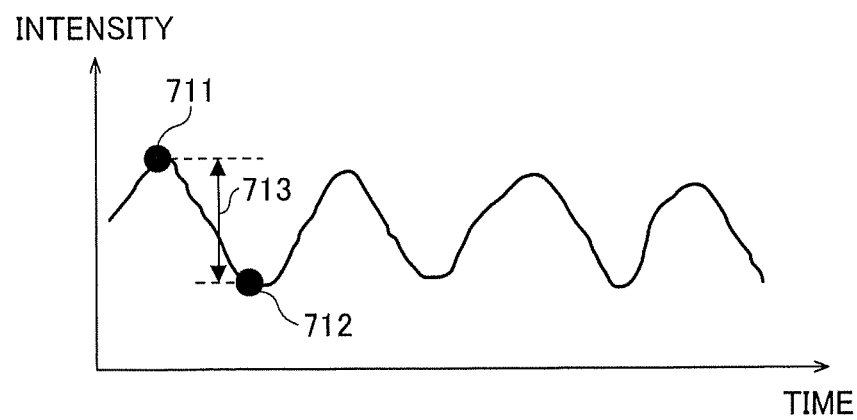
FIG. 10 is a diagram for explaining an example of a process of extracting a time-sequenced waveform of the breath of a living organism.

Example 2 for Extraction of a Time-Sequenced Waveform of the Breath of a Living Organism Hereafter, with reference to FIG. 10, a process of extracting, by the detection unit 13, a time-sequenced waveform of the breath of a living organism in step S6 is described, by way of example. FIG. 10 is a diagram for explaining an example of a process of extracting a time-sequenced waveform of the breath of a living organism.

The detection unit 13 may determine whether or not a given time-sequenced waveform is a time-sequenced waveform of the breath of a living organism based on a largest value and a smallest value of intensity in the given time-sequenced waveform, and extract it. In this case, for example, for each of time-sequenced waveforms with respect to respective distances, the detection unit 13 may calculate a difference between a largest value and a smallest value of intensity in a predetermined period, determine that a time-sequenced waveform in which the difference is equal to or greater than a predetermined threshold value is a time-sequenced waveform of the breath of a living organism, and extract it. In FIG. 10, as an example, a difference 713 between a largest value 711 and a smallest value 712 in a predetermined period of a given time-sequenced waveform with respect to a predetermined distance is indicated.

Figure 11A:
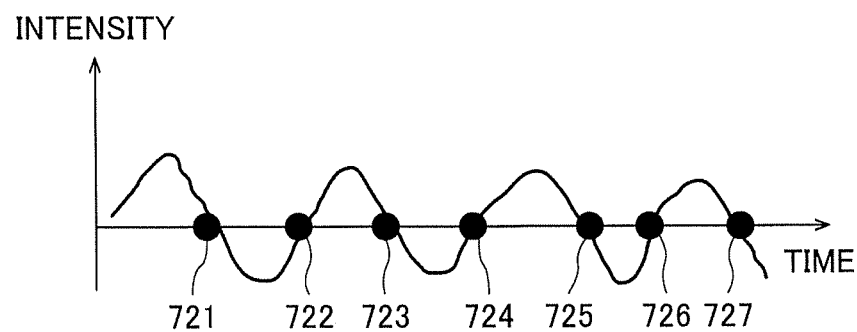
FIGS. 11A and 11B are diagrams for explaining an example of a process of extracting a time-sequenced waveform of the breath of a living organism.
Figure 11B:
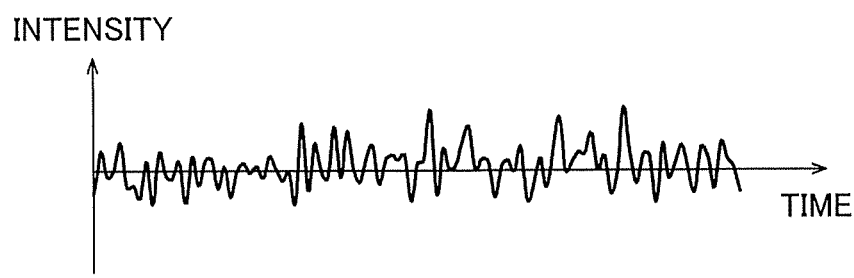

Example 3 for Extraction of a Time-Sequenced Waveform of the Breath of a Living Organism Hereafter, with reference to FIGS. 11A and 11B, a process of extracting, by the detection unit 13, a time-sequenced waveform of the breath of a living organism in step S6 is described, by way of example. FIGS. 11A and 11B are diagrams for explaining an example of a process of extracting a time-sequenced waveform of the breath of a living organism.

For each of time-sequenced waveforms with respect to respective distances, the detection unit 13 corrects each zero-point in such a manner that an average value of intensity of a given time-sequenced waveform in a predetermined period is zero, or the like, for example, and may determine the presence or absence of breathing based on the number of times that the value of intensity in the predetermined period has changed (crossed) to a value other than zero. In this case, as an example, the detection unit 13 may convert the number of times of crossing in the predetermined period into a frequency or a cycle, determine that a time-sequenced waveform in a range of frequencies (e.g., 0.15 Hz to 0.5 Hz) or cycles in breath of a living organism is a time-sequenced waveform of the breath of a living organism, and extract it. In FIG. 11A, as an example of a given time-sequenced waveform of the breath of a living organism, points in time 721 to 727 of crossing zero after the zero-point correction are indicated. When a frequency at each of the points in time 721 to 727 is in a range of frequencies in breath of a living organism, it is determined that a given time-sequenced waveform is a time-sequenced waveform of the breath of a living organism. In FIG. 11B, as an example, a waveform affected by noise or the like is indicated. With respect to such a waveform, a frequency at each of the points in time of crossing zero after zero-point correction is not in a range of frequencies in breath of a living organism. Accordingly, it is determined that a given time-sequenced waveform is not a time-sequenced waveform of the breath of a living organism.

Note that it is possible to combine the above processes of extracting a time-sequenced waveform of the breath of a living organism. For example, the detection unit 13 may determine that a given time-sequenced waveform, in which the difference between the greatest value and the smallest value of intensity, as illustrated in FIG. 10, is equal to or greater than a predetermined value and, further, in which the frequency or the cycle in crossing zero after the zero-point correction, as illustrated in FIG. 11A, is in a range of frequencies or cycles in breath of a living organism, is a time-sequenced waveform in the breath of a living organism, and extract it. Alternatively, the detection unit 13 may set, as an evaluation value, the difference between the greatest value and the smallest value of intensity, as illustrated in FIG. 10, and determine that a given time-sequenced waveform is a time-sequenced waveform of the breath of a living organism to extract it, when a value through multiplication of the evaluation value with a weight coefficient, which corresponds to a degree of coincidence that each frequency or cycle in crossing zero after the zero-point correction as illustrated in FIG. 11A is a frequency or a cycle in breath of a living organism, is equal to or greater than a predetermined threshold value.

Figure 12:
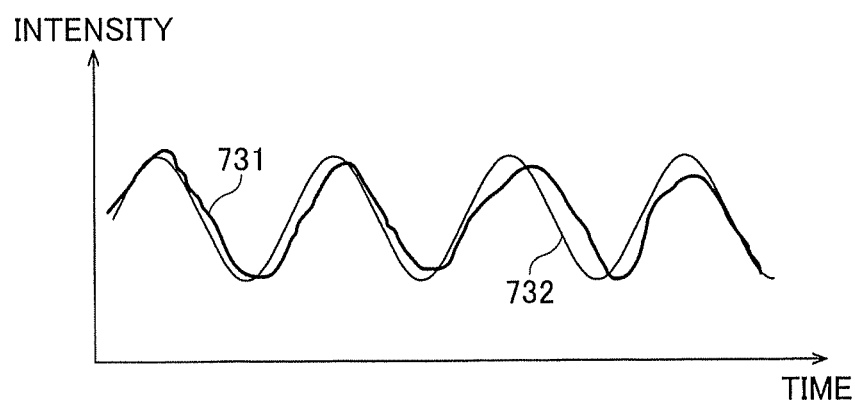
FIG. 12 is a diagram for explaining an example of a process of extracting a time-sequenced waveform of the breath of a living organism.

Example 4 for Extraction of a Time-Sequenced Waveform of the Breath of a Living Organism Hereafter, with reference to FIG. 12, a process of extracting, by the detection unit 13, a time-sequenced waveform of the breath of a living organism in step S6 is described, by way of example. FIG. 12 is a diagram for explaining an example of a process of extracting a time-sequenced waveform of the breath of a living organism.

The detection unit 13 may match each of time-sequenced waveforms with respect to respective distances to one or more ideal breath waveforms, which are preliminarily stored, or sine wave(s) (sinusoidal wave(s)) with a particular cycle, and determine whether or not a given time-sequenced waveform is a time-sequenced waveform of the breath of a living organism. In this case, for example, the detection unit 13 may calculate a coefficient of correlation between a given time-sequenced waveform and each of the preliminarily stored waveforms, and determine the given time-sequenced waveform is a time-sequenced waveform of the breath of a living organism to extract it, when a value of the calculated coefficient of correlation is equal to or greater than a predetermined threshold value.

Note that it is possible to combine the above processes of extracting a time-sequenced waveform of the breath of a living organism. For example, in a case where the difference between the greatest value and the smallest value of intensity, as illustrated in FIG. 10, is equal to or greater than a predetermined value and further a value of a coefficient of correlation with each of the preliminarily stored waveforms, as illustrated in FIG. 12, is equal to or greater than a predetermined threshold value, the detection unit 13 may determine a given time-sequenced waveform is a time-sequenced waveform of the breath of a living organism, and extract it. Thereby, a target time-sequenced waveform to be matched is restricted to waveform(s) that satisfy a condition on a difference between a greatest value and a smallest value, etc. and thus processing time can be decreased.

Figure 13A:
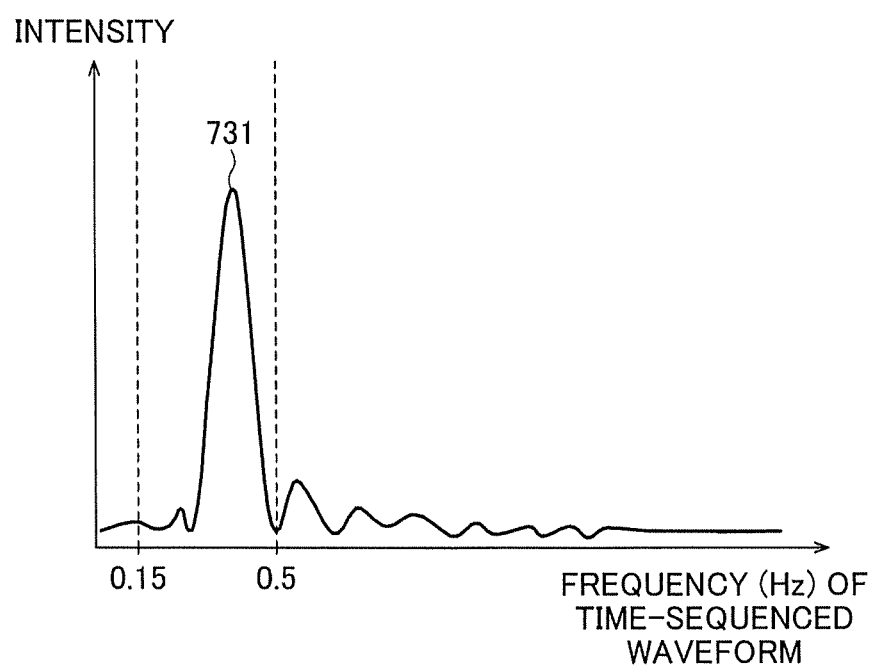
FIGS. 13A and 13B are diagrams for explaining an example of a process of extracting a time-sequenced waveform of the breath of a living organism.
Figure 13B:
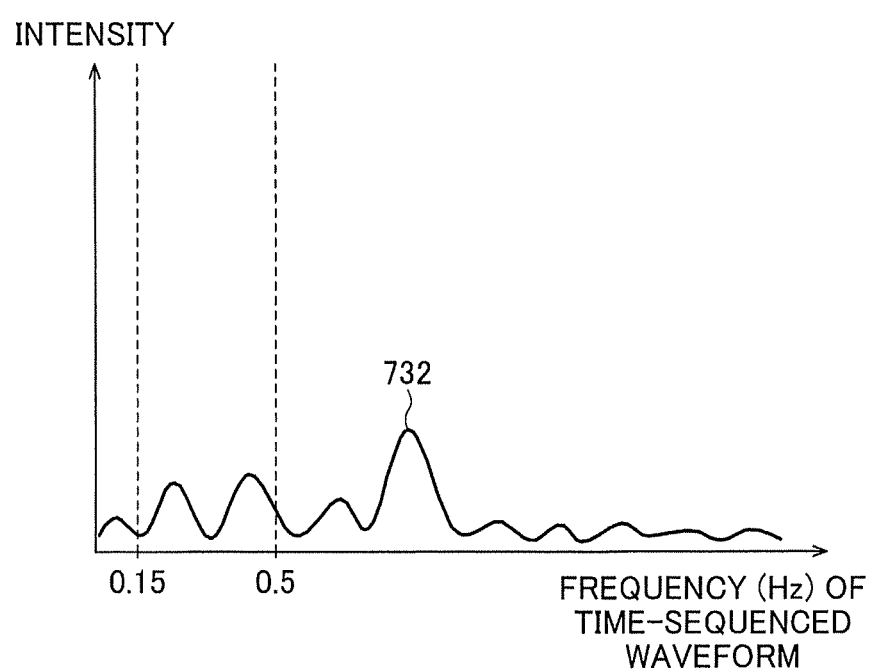

Example 5 for Extraction of a Time-Sequenced Waveform of the Breath of a Living Organism Hereafter, with reference to FIGS. 13A and 13B, a process of extracting, by the detection unit 13, a time-sequenced waveform of the breath of a living organism in step S6 is described, by way of example. FIGS. 13A and 13B are diagrams for explaining an example of a process of extracting a time-sequenced waveform of the breath of a living organism.

The detection unit 13 may use a fast Fourier transform of time-sequenced waveforms with respect to respective distances to determine that a given time-sequenced waveform having a peak of intensity in a range of frequencies (e.g., 0.15 Hz or more to 0.5 Hz or less) in breath of a living organism is a time-sequenced waveform of the breath of a living organism, and extract it.

In FIG. 13A, as an example of a time-sequenced waveform of the breath of a living organism, a peak of intensity in a case of using a fast Fourier transform is indicated. In FIG. 13A, a peak 731 is in a range of frequencies in breath of a living organism, and thus it is determined that a given time-sequenced waveform is a time-sequenced waveform of the breath of a living organism.

In FIG. 13B, as an example of a time-sequenced waveform affected by noise or the like, a peak of intensity in a case of using a fast Fourier transform is indicated. In FIG. 13B, a peak 732 is not in a range of frequencies in breath of a living organism, and thus it is not determined that a given time-sequenced waveform is not a time-sequenced waveform of the breath of a living organism.

Note that it is possible to combine the above processes of extracting a time-sequenced waveform of the breath of a living organism.

According to the present embodiment, with respect to each distance from the sensor 20, it is possible to determine whether or not a given time-sequenced waveform is a time-sequenced waveform of the breath of a living organism. Accordingly, even in a case where a certain living organism and another living organism (e.g., a family member, a dog, a cat, etc.), which is positioned away farther from the sensor 20 than the certain living organism, sleep side by side, respiration of the certain living organism can be detected, as well as avoiding false detection in which respiration of the other living organism is detected as respiration of the certain living organism.

Second Embodiment

Next, a second embodiment is described. In the second embodiment, with use of the detection apparatus 1 according to the first embodiment, detection of loitering or the like is described, by way of example.

Note that, except for a part, the second embodiment is same as the first embodiment; accordingly, explanation may be omitted as appropriate. In the following, a portion common to the first embodiment will be omitted, and only different portions will be described. Note that description in the second embodiment is also applicable to the first embodiment.

<Processing>

Figure 15:
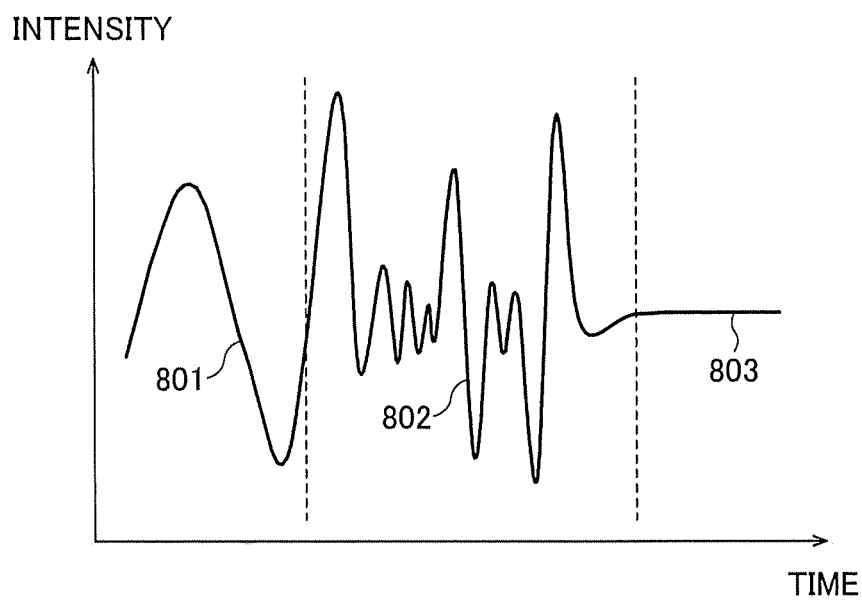
FIG. 15 is a diagram for explaining a time-sequenced waveform affected by an action such as rising.

Hereafter, processing by the detection apparatus 1 is described with reference to FIGS. 14 and 15. FIG. 14 is a flowchart illustrating an example of processing by the detection apparatus 1. FIG. 15 is a diagram for explaining a time-sequenced waveform affected by an action such as arising.

In step S201, the detection unit 13 detects respiration of a living organism at a predetermined distance based on a time-sequenced waveform with respect to each distance.

Subsequently, the detection unit 13 determines whether a time-sequenced waveform affected by an action such as arising at the predetermined distance is detected, based on a time-sequenced waveform with respect to the predetermined distance (step S202).

When an action such as arising at the predetermined distance is detected (YES in step S202), the detection unit 13 determines whether respiration of a living organism at the predetermined distance is detected based on a subsequent time-sequenced waveform with respect to the predetermined distance (step S203).

When respiration of a living organism is detected (YES in step S203), the detection unit 13 waits for a certain period of time, and proceeds to the process in step S202.

When respiration of a living organism is not detected (NO in step S203), the detection unit 13 determines loitering (step S204), and then finishes the process. Note that, in a case of determining loitering, a notification or the like may be sent to a predetermined device, for example. For a given time-sequenced waveform with respect to a predetermined distance illustrated in FIG. 15, after detecting a waveform 801 of the breath of a living organism, in a case where a different waveform from a breath waveform, e.g., a waveform 802 of which the amplitude is same as a breath waveform and of which the cycle is different from a breath waveform is detected and subsequently a waveform 803 of which the amplitude is equal to or smaller than a predetermined threshold value is detected, loitering is determined. Thereby, for example, in a care facility, it is possible to inform a caregiver that a care receiver has risen from a bed and started loitering.

Further, in a case where a distance corresponding to a time-sequenced waveform of the breath of a living organism changes depending on time, the detection unit 13 may determine loitering since it is able to be determined that a living organism has moved.

When an action such as arising is not detected (NO in step S202), the detection unit 13 determines whether respiration of a living organism at the predetermined distance is detected based on a subsequent time-sequenced waveform with respect to the predetermined distance (step S205).

When respiration of a living organism is detected (YES in step S205), the detection unit 13 waits for a certain period of time, and then proceeds to the process in step S202.

When respiration of a living organism is not detected (NO in step S205), the detection unit 13 determines whether respiration of a living organism in proximity to a predetermined distance is detected within a predetermined period, based on a subsequent time-sequenced waveform with respect to the predetermined distance as well as a time-sequenced waveform with respect to a distance in a predetermined range (e.g., 60 cm or less) from the predetermined distance (step S206).

When respiration of a living organism in proximity to a predetermined distance is detected within a predetermined period (YES in step S206), the detection unit 13 determines an apnea state (step S207), and proceeds to the process in step S202.

When respiration of a living organism in proximity to a predetermined distance is not detected within a predetermined period (NO in step S206), the detection unit 13 determines that a given living organism is in a danger state such as cardiopulmonary arrest (step S208), and finishes the process. Note that, in a case of determining that a given living organism is in a danger state, for example, a notification or the like may be sent to a predetermined device.

Third Embodiment

Next, a third embodiment is described. In the third embodiment, with use of the detection apparatus 1 according to the first embodiment, detection of a state of a driver for a vehicle or the like is described, by way of example.

Note that, except for a part, the third embodiment is same as the first embodiment; accordingly, explanation may be omitted as appropriate. In the following, a portion common to the first embodiment will be omitted, and only different portions will be described. Note that description in the third embodiment is also applicable to the first embodiment and the second embodiment.

Figure 16:
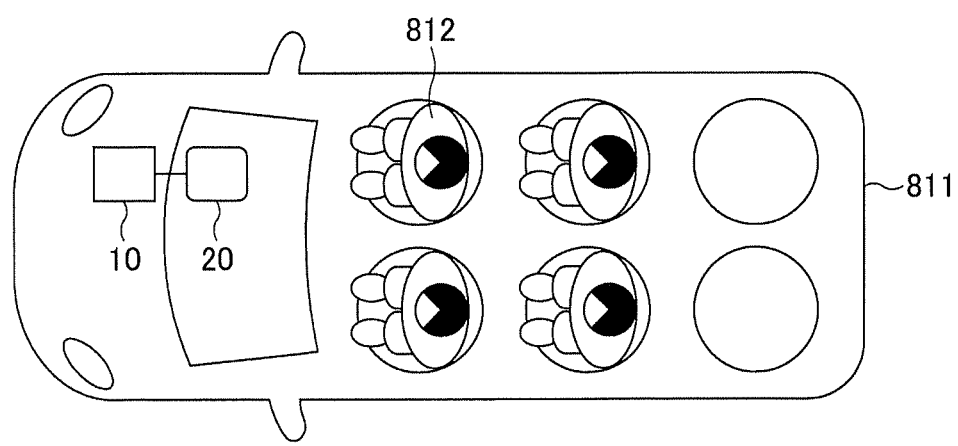
FIG. 16 is a diagram for explaining an example of installing a sensor on a mobile object such as a vehicle.

FIG. 16 is a diagram for explaining an example of installing a sensor 20 on a mobile object such as a vehicle. As illustrated in FIG. 16, the sensor 20 is disposed in proximity of a driver seat 812, e.g., at a location of a handle, a velocity meter, a sun visor for a driver, or the like.

When determining that time-sequenced waveforms with respect to respective distances are each time-sequenced waveforms of the breath of a living organism, the detection unit 13 extracts, as a time-sequenced waveform of the breath of the living organism, only a time-sequenced waveform with respect to a closest distance from the sensor 20.

In a conventional radio sensor, if there are other passenger(s) other than a driver, it may fail to observe respiration of the driver due to influence on reflected wave(s) from the other passenger(s). On the other hand, in the present embodiment, by extracting a time-sequenced waveform with respect to a closest (shortest) distance to the sensor 20, among time-sequenced waveforms that are each determined as a time-sequenced waveform of breath, it is possible to suppress influence on reflected wave(s) from the other passenger(s) and thus observe a time-sequenced waveform of the breath of a driver. Accordingly, based on a time-sequenced waveform of the breath of a driver, it is possible to determine whether or not the driver is sleepy or tired, and whether or not the driver is in a danger status such as cardiopulmonary arrest. In this case, for example, a coefficient of correlation between the detected time-sequenced waveform of the breath and a preliminarily stored time-sequenced waveform relating to drowsiness or fatigue is calculated. When a value of the calculated coefficient of correlation is equal to or greater than a predetermined threshold value, it may be determined that the driver is sleepy or tired. In determining that a driver is in a danger status, a similar process to the second embodiment described above may be executed, by way of example.

Fourth Embodiment

Next, a fourth embodiment is described. In the fourth embodiment, with use of the detection apparatus 1 according to the first embodiment, detection of respiration of a human body in a bath is described, by way of example.

Note that, except for a part, the fourth embodiment is same as the first embodiment; accordingly, explanation may be omitted as appropriate. In the following, a portion common to the first embodiment will be omitted, and only different portions will be described. Note that description in the fourth embodiment is also applicable to the first embodiment, the second embodiment, and the third embodiment.

Figure 17:
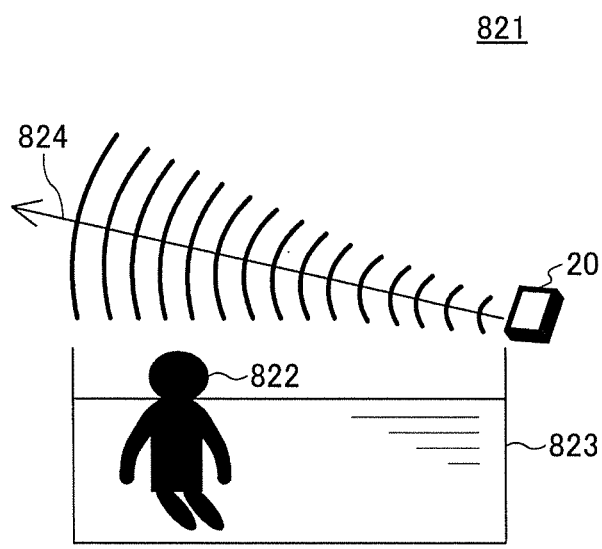
FIG. 17 is a diagram for explaining an example of installing a sensor in a bathroom.

FIG. 17 is a diagram illustrating an example of installing a sensor 20 in a bathroom. As illustrated in FIG. 17, in a bathroom 821, a sensor 20 is located in proximity of a person in bath 822. Note that as illustrated in FIG. 17, the sensor 20 is provided around a bathtub 823, e.g., on an edge of the bathtub, and the middle 824 of radiation directions of radio waves from the sensor 20 may be directed upwardly with respect to an upper side of the bathtub 823, i.e., relative to a horizontal direction. Thereby, influence on reflected waves on a surface of water can be suppressed.

In a conventional radio-frequency sensor, reflected waves from water in a bathtub have relatively high intensity, and thus observation for the presence or absence of breathing or a respiratory state of a human body may fail. On the other hand, according to the present embodiment, in light of the fact that a head positioned above a surface of water in the bathtub moves responsive to breathing, the presence or absence of breathing of a human body during bathing is able to be detected based on time-sequenced waveforms affected by movements of the head. Thereby, based on time-sequenced waveform(s) of breath of a person who takes a bath, it is possible to determine whether or not the person is drowning, and whether or not the person is in a danger status such as cardiopulmonary arrest due to heat shock or the like.

Fifth Embodiment

Next, a fifth embodiment is described. In the fifth embodiment, explanation will be provided for a case where data detected by the detection apparatus 1 according to the first embodiment is stored in a server and can be displayed by a terminal, by way of example.

Note that, except for a part, the fifth embodiment is same as the first embodiment; accordingly, explanation may be omitted as appropriate. In the following, a portion common to the first embodiment will be omitted, and only different portions will be described. Note that description in the fifth embodiment is also applicable to the first embodiment, the second embodiment, the third embodiment, and the fourth embodiment.

Figure 18:
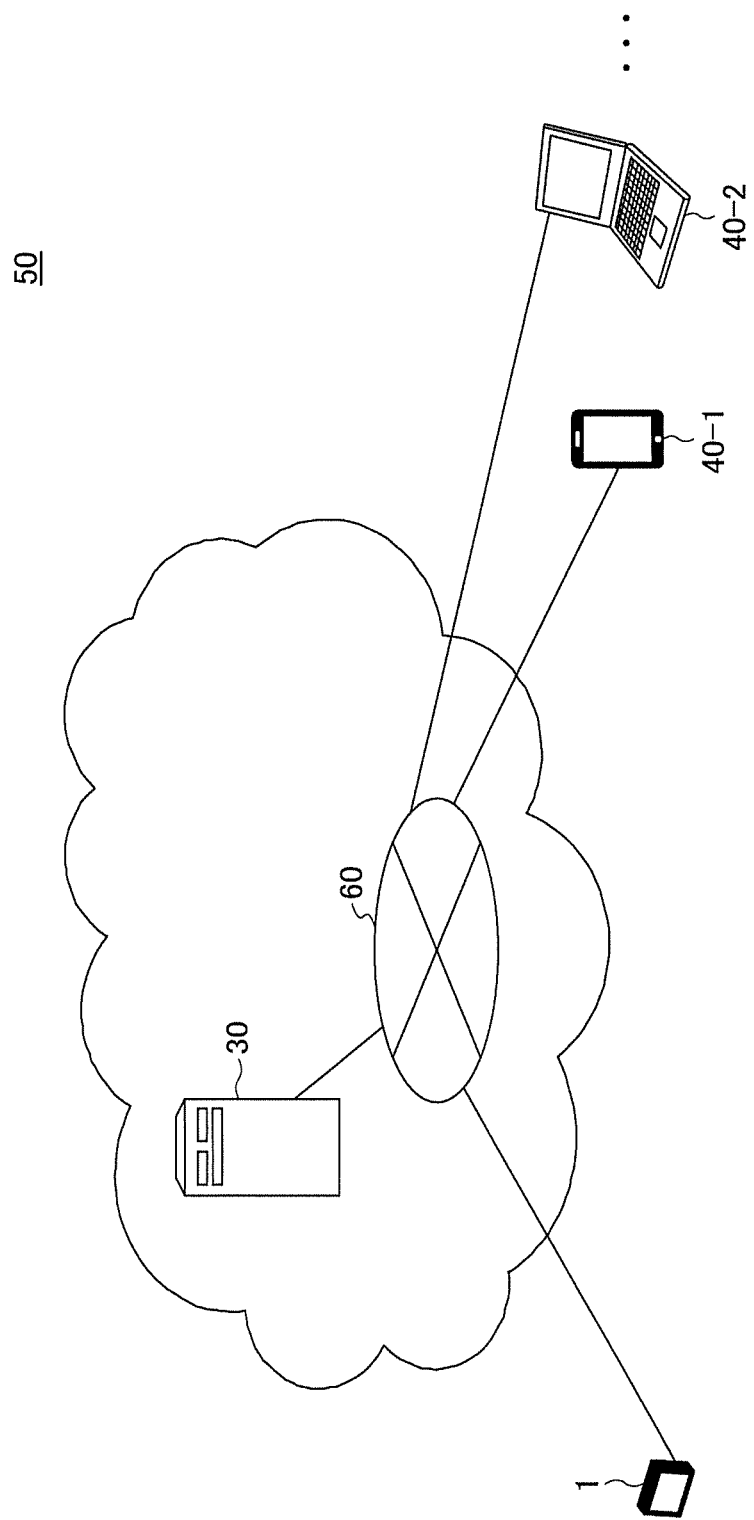
FIG. 18 is a diagram illustrating an example of an information processing system that includes the detection apparatus.

FIG. 18 is a diagram illustrating an example of an information processing system 50 that includes a detection apparatus 1. The information processing system 50 includes the detection apparatus 1, a server 30, terminals 40-1, 40-2, . . . (in the following description, when it is not necessary to distinguish between these terminals, they are simply referred to as "terminals 40").

The detection apparatus 1, the server 30, and terminals 40 are coupled so as to be capable of communicating via a network 60, such as a LAN (local area network), a wireless LAN, Bluetooth (registered trademark), a mobile phone network, or/and the Internet.

The server 30 is an information processing apparatus (computer) for use as a server, and stores data indicated by the detection apparatus 1, the data being associated with identification information for the detection apparatus 1, for example.

Each terminal 40 is an information processing apparatus, such as a desktop PC (Personal Computer), a notebook PC, a tablet PC, or a smartphone. Each terminal 40 logs in to the server 30, and displays data or the like relating to respiration or a status, detected by the detection apparatus 1.

Thereby, data such as the presence or absence of breathing, loitering or cardiopulmonary arrest of a living organism can be checked using a terminal 40 via the server 30 in the cloud, for example. Note that a terminal 40 may be able to display data acquired directly from the detection apparatus 1 without using the server 30. In addition, the detection apparatus 1 may send, to a terminal 40, a notification of loitering, cardiopulmonary arrest or the like.

<Other>

In each of the above embodiments, explanation has been provided for the case where a human body as a living organism is the subject, by way of example. However, a living organism of an animal other than a human being, such as a dog or a cat, may be the subject. For example, in a case of installing a sensor 20 in a field, a mountain forest, or the like, by recognizing respiration of appearing wildlife, it is possible to detect wildlife. In this case, with the detection apparatus 1 according to the embodiments, it is possible to check if wildlife is present, as well as suppressing effects of plant(s) moving due to winds or of rainwater, etc.

The embodiments according to the present disclosure have been described above in detail, but the present disclosure is not limited to such specific embodiments. Various modifications and changes can be made within a scope of the spirit of the present disclosure as set forth in the claims.

Each functional unit of the information processing apparatus 10 may be implemented by cloud computing that has one or more computers, for example. The information processing apparatus 10 and the sensor 20 may also be configured as an integrated device. At least part of functional units of the information processing apparatus 10 may be provided with the sensor 20. At least part of functional units of the sensor 20 may be provided with the information processing apparatus 10.

What is claimed is:

1. An information processing apparatus comprising:
a circuit configured to:
calculate distance spectra based on a beat signal being a difference between a transmitted wave, which is a radio wave that is transmitted by a sensor and that is swept in frequency, and a reflected wave of the transmitted wave, the reflected wave being received by the sensor, and configured to calculate one or more time-sequenced waveforms each indicating time changes in intensity of the distance spectra with respect to respective distances from the sensor;
calculate, with respect to a given one among the one or more time-sequenced waveforms, a first value being an absolute value of a difference between intensity of the distance spectrum at a first point in time and intensity of the distance spectrum at a second point in time different from the first point, and to calculate a second value being an absolute value of a difference between intensity of the distance spectrum at a third point in time and intensity of the distance spectrum at a fourth point in time different from the third point; and
detect respiration of a living organism based on a total of the first value and the second value.

2. The information processing apparatus according to claim 1, wherein the circuit is configured to output, as a breath waveform of the living organism, at least one time-sequenced waveform that satisfies a predetermined condition, among the one or more time-sequenced waveforms with respect to respective distances from the sensor.

3. The information processing apparatus according to claim 1, wherein the circuit is configured to output, as a distance to the living organism, a distance corresponding to at least one time-sequenced waveform that satisfies a predetermined condition, among the one or more time-sequenced waveforms with respect to respective distances from the sensor.

4. The information processing apparatus according to claim 1, wherein the one or more time-sequenced waveforms include a plurality of time-sequenced waveforms that each satisfy a predetermined condition, and
the circuit is configured to output, as a breath waveform of the living organism, a time-sequenced waveform with respect to a closest distance to the sensor, among a plurality of time-sequenced waveforms.

5. The information processing apparatus according to claim 1, wherein the second point in time is set after the first point in time, and the fourth point in time is set after the third point in time.

6. The information processing apparatus according to claim 1, wherein the circuit is configured to detect respiration of the living organism based on a difference between a largest value and a smallest value of intensity of a distance spectrum in a predetermined period of the given one among the one or more time-sequenced waveforms.

7. The information processing apparatus according to claim 1, wherein the circuit is configured to detect respiration of the living organism based on a wave frequency or a wave cycle derived from the given one among the one or more time-sequenced waveforms.

8. The information processing apparatus according to claim 1, wherein the circuit is configured to detect respiration of the living organism based on a coefficient of a correlation between a wave from the given time-sequenced waveform and a predetermined wave.

9. The information processing apparatus according to claim 1, wherein the circuit is configured to use a Fourier transform of the one or more time-sequenced waveforms to detect respiration of the living organism based on intensity of a distance spectrum with respect to each frequency of the one or more time-sequenced waveforms.

10. The information processing apparatus according to claim 1, wherein the circuit is configured to detect a movement of the living organism or a respiratory arrest status of the living organism, based on the given time-sequenced waveform relating to the detected respiration of the living organism.

11. A detection apparatus comprising:
- a sensor configured to transmit a transmitted wave being a radio wave that is swept in frequency, and receive a reflected wave of the transmitted wave;
- a circuit configured to:
  - calculate distance spectra based on a beat signal being a difference between the transmitted wave and the reflected wave, and calculate one or more time-sequenced waveforms each indicating time changes in intensity of the distance spectra with respect to respective distances from the sensor;
  - calculate, with respect to a given one among the one or more time-sequenced waveforms, a first value being an absolute value of a difference between intensity of the distance spectrum at a first point in time and intensity of a distance spectrum at a second point in time different from the first point, and to calculate a second value being an absolute value of a difference between intensity of a distance spectrum at a third point in time and intensity of a distance spectrum at a fourth point in time different from the third point; and
  - detect respiration of a living organism based on a total of the first value and the second value.

* * * * *